United States Patent [19]
Fankhauser et al.

[11] Patent Number: 5,814,341
[45] Date of Patent: Sep. 29, 1998

[54] COSMETIC COMPOSITIONS

[75] Inventors: Peter Fankhauser, Ettingen, Switzerland; Thomas Maier, Schliengen, Germany

[73] Assignee: Ciba Specialty Chemicals Corporation, Tarrytown, N.Y.

[21] Appl. No.: 693,061

[22] PCT Filed: Feb. 6, 1995

[86] PCT No.: PCT/EP95/00408

§ 371 Date: Aug. 12, 1996

§ 102(e) Date: Aug. 12, 1996

[87] PCT Pub. No.: WO95/22310

PCT Pub. Date: Aug. 24, 1995

[30] Foreign Application Priority Data

Feb. 18, 1994 [GB] United Kingdom ............... 94031531

[51] Int. Cl.$^6$ ..................................... A61K 9/16
[52] U.S. Cl. ................. 424/493; 106/205; 106/208; 252/315.3; 351/160 H; 424/492; 424/496; 424/500; 536/1.1; 536/4.1; 536/115; 536/123; 536/124
[58] Field of Search ................... 424/493, 492, 424/496, 500; 351/150 H; 106/205, 208; 252/315.3; 536/1.1, 4.1, 115, 123, 124

[56] References Cited

U.S. PATENT DOCUMENTS

| | | | |
|---|---|---|---|
| 3,507,290 | 4/1970 | Halleck | 424/401 |
| 3,659,025 | 4/1972 | Halleck | 424/401 |
| 4,774,093 | 9/1988 | Provonchee et al. | 424/493 |
| 4,946,450 | 8/1990 | Erwin | 604/294 |
| 5,084,386 | 1/1992 | Lusé et al. | 435/101 |
| 5,135,920 | 8/1992 | Kanamaru et al. | 514/59 |
| 5,158,772 | 10/1992 | Davis | 424/401 |
| 5,223,491 | 6/1993 | Donzis | 514/54 |

FOREIGN PATENT DOCUMENTS

| | | |
|---|---|---|
| 0504673 | 9/1992 | European Pat. Off. . |
| 2050825 | 1/1981 | United Kingdom . |
| 2176795 | 1/1987 | United Kingdom . |
| 90/12106 | 10/1990 | WIPO . |

OTHER PUBLICATIONS

Derwent Abstracts, 91–306708/42.
Derwent Abstracts, 91–256625/35.
Derwent Abstracts, 91–048838.
Derwent Abstract, 90–217294.
JAP10 No. 03464823.
Patent Abstracts of Japan, vol. 12, No. 59 (C–478), Publication No. JP 62205008 (1987).

*Primary Examiner*—Terressa Mosley
*Attorney, Agent, or Firm*—Kevin T. Mansfield

[57] ABSTRACT

A cosmetic composition is provided comprising:
A) a cosmetically acceptable carrier; and
B) 0.05 to 3.0% by weight, based on the weight of the total composition, of a β-1,3-glucan having a mean molecular weight of $10^5$ to $25.10^6$.

23 Claims, No Drawings

COSMETIC COMPOSITIONS

The present invention relates to cosmetic compositions and, in particular, to such compositions containing a glucan as an active ingredient.

In GB-A-2 050 825 there is described a skin cosmetic composition of the oil-in-water type, comprising an emulsifying agent, an oil and water, the emulsifying agent being composed of a) at least one specified glycyrrhizic compound and b) at least one water-soluble polysaccharide selected from pectin, karaya gum, locust bean gum and xanthan gum.

The polysaccharides used in GB-A-2 050 825 have certain disadvantages, namely that they contain acidic groups, rendering them sensitive to salt formation and/or variations in pH, as well as a lack of stability over an adequate temperature range.

In JP 030167109 there is described a cosmetic material containing a β-1,3-glucan having a mean molecular weight greater than $10.10^6$. β-1,3-glucans having a mean molecular weight greater than $10.10^6$, however, are of poor aspect, and their molecular weight cannot be determined using the conventional light scattering method.

It has now been found that certain glucans are useful as active ingredients and as excipients in cosmetic compositions, without the disadvantages associated with the polysaccharides used in GB-A-2 050 825 or with the β-1,3-glucans of JP 030167109. Moreover, the glucans used in the present compositions, on drying, form flexible films which, although insoluble in water, swell readily therein. This ability to form films represents an added advantage for the use of these glucans in cosmetic formulations:

Accordingly, the present invention provides a cosmetic composition comprising:

A) a cosmetically acceptable carrier; and

B) 0.05 to 3.0, preferably 0.2 to 1.0% by weight; based on the weight of the total composition, of a β-1,3-glucan having a mean molecular weight of $10^5$ to $10.10^6$, preferably 2 to $10.10^6$.

The cosmetic composition may constitute, e.g., a shampoo and/or hair conditioner composition, in which the glucan component B) may perform one or more of the following functions:

i) effect an improvement in the combability of hair treated with the shampoo/conditioner;

ii) effect an improvement in the dispersion of other components in the shampoo/conditioner;

iii) act as a smoothing agent for hair treated with the shampoo/conditioner; and iv) effect an improvement in the level of fixing of such additives as dyes or UV absorbers in the shampoo/conditioner.

The cosmetic composition according to the present invention may also constitute a skin care composition, e.g., an emulsion or cream in which the glucan may perform one or more of the following functions:

i) effect a lubricating function, thereby facilitating the spreading of the composition on the skin;

ii) act as a film-forming agent, thereby providing a protective film on the skin, which film, while almost undetectable by touching, provides the skin with a silky feel;

iii) effect a smoothing of the skin by reducing the scaling of the outermost layer of stratum corneum;

iv) effect an improvement in the dispersion of other components of the skin care composition; and v) act as an emulsifier or co-emulsifier for the skin care composition.

The skin care composition may be formulated as an aqueous lotion, a water-in-oil or an oil-in-water emulsion, an oil or oil-alcohol lotion, a vesicular dispersion of anionic or nonionic amphiphilic lipids, an aqueous, aqueous-alcohol, alcohol or oil-alcohol gel, a solid stick or an aerosol formulation.

When formulated as a water-in-oil or an oil-in-water emulsion, the cosmetically acceptable carrier A) preferably comprises 5 to 50% of an oil phase; and 47 to 94.95% of water, each based on the total weight of the composition.

The oil phase may comprise any oil, or mixture thereof,. which is known to be suitable for use in cosmetic compositions.

Examples of such oils include aliphatic hydrocarbons such as liquid paraffin, squalane, vaseline and ceresin; vegetable oils such as orive oil, almond oil, sesame oil, avocado oil, castor oil, cacao butter and palm oil; animal oils such shark liver oil, cod liver oil, whale oil, beef tallow and butter fat; waxes including bees wax, carnauba wax, spermaceti and lanolin; fatty acids such as lauric acid, myristic acid, , palmitic acid, stearic acid, oleic acid and behenic acid; aliphatic alcohols such as lauryl alcohol, stearyl alcohol, cetyl alcohol and oleyl alcohol; and aliphatic esters such as isopropyl-, isocetyl- or octadecyl myristate, butyl stearate, hexyl laurate, diisopropyl adipate or diisopropyl sebacate.

Preferred mono- or polyols, for use in an oil-alcohol lotion, or a an oil-alcohol or alcohol gel, include ethanol, isopropanol, propylene glycol, hexylene glycol, glycerine and sorbitol.

When the β-1,3-glucan is used as a co-emulsifier, the other emulsifier used may be any emulsifier conventionally used in cosmetic formulations e.g., one or more of an ethoxylated ester of a natural oil derivative such as a polyethoxylated ester of hydrogenated castor oil; a silicone oil emulsifier such as a silicone polyol; an optionally ethoxylated fatty acid soap; an ethoxylated fatty alcohol; an optionally ethoxylated sorbitan ester, an ethoxylated fatty acid; or an ethoxylated glyceride.

The cosmetic composition according to the present invention may also constitute an oral care preparation, e.g., a dental gel, a denture fixation aid, a tooth paste, a mucosal lubricant formulation such as a vaginal cream or gel, or an ophthalmological preparation such as eye drops, in which the glucan component B) may perform one or more of the following functions:

i) effect lubrication of dry mucosae;

ii) effect thickening of liquid preparations;

iii) effect retention of active ingredients by formation of films on mucosal surfaces; and iv) effect an improvement in the dispersion of other components in the composition.

When the β-1,3-glucan is used in an ophthalmological preparation, it may be used together with other components such as:

a) ophthalmological active ingredients e.g. Gentamicin sulphate, Lomefloxacin hydrochloride, Chloramphenicol, Sodium Diclofenac, Potassium Diclofenac, Dexamethason di-sodium phosphate, Naphazolin nitrate, Tetryzolin hydrochloride, Antazolin hydrochloride, Antazolin sulphate, Pilocarpin chloride, Vitamin A-palmitate and zinc sulphate;

b) ophthalmological buffers such as boric acid, borax, acetic acid, sodium acetate, phosphoric acid, sodium dihydrogen phosphate, disodium hydrogen phosphate, sodium phosphate, Trometamol, citric acid and sodium citrate;

c) ophthalmological preservatives such as benzyl alkylammonium chloride, benzoxonium chloride, chlorhexidine digluconate, chlorobutanol, phenylethyl alcohol and Thiomersal;
d) solvents such as ethanol, glycerol, polyethylene glycol and water;
e) solution aids such as Cremophor EL, Cremophor RH, Tween 20 and Tween 80;
f) isotonising agents such as sodium chloride, mannitol and sorbitol,
g) chelate formers such as disodium EDTA;
h) antioxidants such as α-tocopherol acetate, ascorbic acid, N-acetyl-cystine, sodium bisulphite, sodium thiosulphate and propyl gallate; and
i) viscosity-increasing compounds such as methylhydroxypropyl cellulose, Carbopol 934 P, Carbopol 940, Carbopol 980 and Polaxomer F 127.

The β-1,3-glucan component of the cosmetic composition of the present invention has the structural formula:

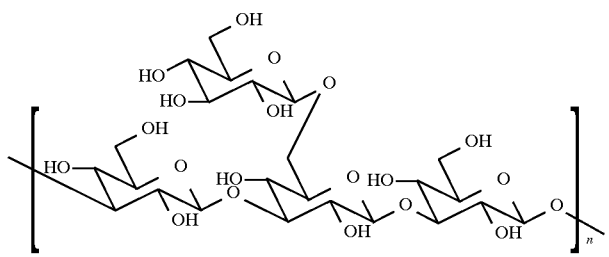

in which n is a number which provides the β-1,3-glucan component with a mean molecular weight (MW) of $10^5$ to $10.10^6$, preferably 2 to $10.10^6$, determined from the readily measured Staudinger Index η using the following Mark-Houwink equation:

$$MW=[\eta/4.45.10^{-7}]^{1/1.49}$$

Preferably, a 0.3 g/l aqueous solution of the β-1,3-glucan has a glucose content below 0.1 g/l and a viscosity of 50 to 190 mPa.s, measured at a shear-rate of 0.3 s$^{-1}$ at 40° C.

The β-1,3-glucan may be produced by any conventional method for the production of a high-molecular, uncharged homopolysaccharide; in particular such a known method using microorganisms.

One preferred method is that described in EP-A-504 673. In this specification, there is described a process for the extra-cellular production of homopolysaccharides of molecular weight ranging from 5 to $25.10^6$, having only β-1,3-D-glucopyranose units in the main chain, each third unit of which is β-1,6-glycosidically bonded with a further glucose unit. The process is characterized in that microorganisms, in the form of at least one of the fungal strains DSM 6318, DSM 6319 and DSM 6320 is cultivated in a culture medium, with aeration and agitation, at 15° to 40° C.; the culture solution is then separated from the mass of cells; and the water-soluble homopolysaccharide so obtained is isolated in conventional manner.

The cosmetic composition of the invention may also comprise further components which are known to perform a useful function in a cosmetic composition. Examples of such further components include, e.g., emollients, skin moisturisers, UV absorbers such as an oxanilide, a triazine or triazole, additional thickening agents such as xanthan, moisture-retention agents such as glycerine, film formers, preservatives, perfumes and colourants.

The following Examples further illustrate the present invention.

EXAMPLE 1

A) Cross-infection of the protoclon B-strain with the monokaryotic strain S.commune ATCC 36481 giving S.commune DSM 6320

Using the procedure described in Example 1 of EP-A-504 673, the cross-infection is effected in Petri dishes, in the middle of which a piece of the micelle of both strains is inoculated at a separation of about 1 cm. The composition of the agar medium corresponds to the complex medium for immersion cultivation (see part B) with an additional 15 g/l of agar. The incubation is effected at room temperature in daylight. As soon as the first spores are visible, after about 10 to 14 days, a stock solution is established from the new dikaryon.

B) Production of glucan component

The new dikaryon DSM 6320, is then immersion cultivated in a 1 litre Erlenmeyer flask in a medium comprising 33 g/l glucose.H$_2$O, 3 g/l technical yeast extract, 1 g/l KH$_2$PO$_4$ and 0.5 g/l MgSO$_4$.7H$_2$O The product obtained after 120 hours has a micelle dry mass (g/l) of 2.5, contains 12.0 g/l of polysaccharide (PS) having a mean molecular weight of $4.10^6$ and has a Y$_{PS/S}$ value (product yield coefficient—g PS/g consumed substrate) of 0.4.

The following Table contains data relating to various physical properties of a β-1,3-glucan used in a cosmetic composition according to the present invention. The respective β-1,3-glucans of mean molecular weight $6.10^6$, $1.10^6$ or $0.1.10^6$ are produced in a manner similar to that set out in Example 1. For the purposes of comparison, the Table also contains data relating a β-1,3-glucan having a mean molecular weight greater than $10.10^6$ according to JP 030167109.

| mol. wt. | $15.10^6$ | $12.10^6$ | $6.10^6$ | $4.10^6$ | $1.10^6$ | $0.1.10^6$ |
|---|---|---|---|---|---|---|
| viscosity at 0.5 g/l and 0.062/s | 1422 | 1079 | 948 | 875 | 755 | 688 |
| aspect light scattering aspect | opaque microgel | opaque microgel | clear microgel free | clear microgel free | clear microgel free | clear microgel free |
| organoleptic feel | gritty | gritty | smooth non-tacky | smooth non-tacky | smooth non-tacky | smooth non-tacky |
| film forming property | stable | stable | stable | stable | stable | |

The distinct and superior viscosity, aspect, light-scattering aspect and organoleptic feel properties of a β-1,3-glucan used in a cosmetic composition according to the present invention, relative to a β-1,3-glucan having a mean molecular weight greater than $10.10^6$ according to JP 030167109, are clear.

EXAMPLE 2

A massage cream is formulated from the following ingredients:

2% bees wax
45% liquid paraffin
3% cetyl alcohol
2.5% pectin (mol. weight 100,000)
46.5% deionised water
0.2% methylparaben
0.5% glucan from Example 1 and 0.3% perfume each by weight, based on the total weight of the cream.

A first solution is prepared by homogeneously dissolving the pectin, methylparaben and glucan in the deionised water at 80° C. A second solution is produced by melting the bees wax, liquid paraffin and cetyl alcohol by heating the mixture to 80° C. While the first solution is stirred in a homomixer, the second solution is added to it and dispersed in it. The resulting emulsion is allowed to cool and, on reaching 70° C., the perfume is added. Stirring is stopped once the temperature falls to 30° C. The oil-in-water form massage cream so obtained has good texture and gloss and is stable at 2°–60° C. over 6 months.

EXAMPLE 3

An aqueous ophthalmological preparation is formulated from the following ingredients:

1 mg Glucan from Example 1
1 mg Sodium Diclofenac
50 mg Solution aid (Cremophor EL)
6 mg Ophthalmological buffer (Trometamol)
19 mg Boric acid
0.04 mg Ophthalmological preservative (Thiomersal)
Water for injection purposes to 1.00 ml.

We claim:

1. A cosmetic composition comprising:
A) a cosmetically acceptable carrier; and
B) 0.05 to 3.0% by weight, based on the weight of the total composition, of a β-1,3-glucan having a mean molecular weight of $2\times10^6$ to $10\times10^6$.

2. A composition according to claim 1 in which the composition constitutes a shampoo and/or hair conditioner composition.

3. A composition according to claim 1 in which the composition is a skin care composition.

4. A composition according to claim 3 in which the skin care composition is formulated as an aqueous lotion, a water-in-oil or an oil-in-water emulsion, an oil or oil-alcohol lotion, a vesicular dispersion of an anionic or nonionic amphiphilic lipid, an aqueous, aqueous-alcohol, alcohol or oil-alcohol gel, a solid stick or an aerosol.

5. A composition according to claim 4 in which, in a water-in-oil or an oil-in-water emulsion, the cosmetically acceptable carrier A) comprises 5 to 50% of an oil phase and 47 to 94.95% of water, each based on the total weight of the composition.

6. A composition according to claim 5 in which the oil phase is an aliphatic hydrocarbon; a vegetable oil; an animal oil; a wax; a fatty acid; an aliphatic alcohol; or an aliphatic ester.

7. A composition according to claim 6 in which the aliphatic hydrocarbon is a liquid paraffin, squalane, vaseline or ceresin; the vegetable oil is olive oil, almond oil, sesame oil, avocado oil, castor oil, cacao butter or palm oil; the animal oil is shark liver oil, cod liver oil, whale oil, beef tallow or butter fat; the wax is bees wax, carnauba wax, spermaceti or lanolin; the fatty acid is lauric acid, myristic acid, palmitic acid, stearic acid, oleic acid or behenic acid; the aliphatic alcohol is lauryl alcohol, stearyl alcohol, cetyl alcohol or oleyl alcohol; and the aliphatic ester is isopropyl-, isocetyl- or octadecyl myristate, butyl stearate, hexyl laurate, diisopropyl adipate or diisopropyl sebacate.

8. A composition according to claim 4 in which the β-1,3-glucan functions as a co-emulsifier for the composition and the other emulsifier used is one or more of an ethoxylated ester of a natural oil derivative; a silicone oil emulsifier, an optionally ethoxylated fatty acid soap; an ethoxylated fatty alcohol; an optionally ethoxylated sorbitan ester; an ethoxylated fatty acid; or an ethoxylated glyceride.

9. A composition according to claim 8 in which the ethoxylated ester of a natural oil derivative is a polyethoxylated ester of hydrogenated castor oil; and the silicone oil emulsifier is a silicone polyol.

10. A composition according to claim 1 in which the composition constitutes an oral care preparation; a mucosal lubricant formulation; or an ophthalmological preparation comprising a carrier.

11. A composition according to claim 10 in which the oral care preparation is formulated as a dental gel, a denture fixation aid or a tooth paste.

12. A composition according to claim 10 in which the mucosal lubricant formulation is a vaginal cream or gel.

13. A composition according to claim 10 in which the ophthalmological preparation is an eye drops preparation.

14. A composition according to claim 1 which the β-1,3-glucan is produced by a process for the extra-cellular production of homopolysaccharides of molecular weight ranging from $10^5$ to $10.10^6$, having only β-1,3-D-glucopyranose units in the main chain, each third unit of which is β-1,6-glycosidically bonded with a further glucose unit, characterized in that microorganisms, in the form of at least one of the fungal strains DSM 6318, DSM 6319 and DSM 6320 is cultivated in a culture medium, with aeration and agitation, at 15° to 40° C.; the culture solution is then separated from the mass of cells; and the water-soluble homopolysaccharide so obtained is isolated in conventional manner.

15. A composition according to claim 1 in which the composition also comprises one or more of emollients, skin moisturisers, UV absorbers, additional thickening agents, moisture-retention agents, film formers, preservatives, perfumes and colourants.

16. A composition according to claim 15 in which the UV absorber is an oxanilide, a triazine or triazole, the additional thickening agent is xanthan and the moisture-retention agent is glycerine.

17. A composition according to claim 10 in which the carrier is an ophthalmological solvent.

18. A composition according to claim 13 which also comprises an ophthalmologically-active ingredient.

19. A composition according to claim 13 which also comprises an ophthalmological buffer.

20. A composition according to claim 13 which also comprises an ophthalmological preservative.

21. A composition according to claim 13 which further comprises at least one of a solution aid, an isotonising agent, a chelate former, an antioxidant or a viscosity-increasing compound.

22. An eye drops preparation which consists of:

0.05 to 3.0% by weight based on the weight of the total composition, of a β-1,3glucan having a means molecular weight of $1\times10^6$ to $10\times10^6$, sodium diclofenac, a solution aid, an opthalmological buffer, boric acid;

an opthalmological preservative and water.

23. A cosmetic composition comprising:

A) a cosmetically acceptable carrier; and

B) 0.2 to 1.0% by weight, based on the weight of the total composition, of a β1,3-glucan having a mean molecular weight of $2\times10^6$ to $10\times10^6$.

* * * * *

UNITED STATES PATENT AND TRADEMARK OFFICE
CERTIFICATE OF CORRECTION

PATENT NO. : 5,814,341
DATED : September 29, 1998
INVENTOR(S) : Peter Fankhauser, et al It is certified that error appears in the above-identified patent and that said Letters Patent is hereby corrected as shown below:

Column 5, claim , line 5, claim, should read:
--molecular weight of $1 \times 10^6$ to $10 \times 10^6$--.

Signed and Sealed this

Thirtieth Day of March, 1999

Attest:

Q. TODD DICKINSON

Attesting Officer

Acting Commissioner of Patents and Trademarks